United States Patent

Blazejak et al.

[11] Patent Number: 5,391,804
[45] Date of Patent: Feb. 21, 1995

[54] PROCESS FOR THE PREPARATION OF MONO-N-β-CYANOETHYLANILINES

[75] Inventors: Manfred Blazejak, Düsseldorf; Wilfried Köhler, Bergisch Gladbach; Karl-Johann Wemmje, Burscheid, all of Germany

[73] Assignee: Bayer Aktiengesellschaft, Leverkusen, Germany

[21] Appl. No.: 189,016

[22] Filed: Jan. 28, 1994

[30] Foreign Application Priority Data

Feb. 4, 1993 [DE] Germany ............... 4303131

[51] Int. Cl.⁶ ................................ C07C 253/30
[52] U.S. Cl. ..................................... 558/394
[58] Field of Search ........................... 558/394

[56] References Cited

U.S. PATENT DOCUMENTS

| 2,492,972 | 1/1950 | Dickey | 260/205 |
| 2,820,051 | 1/1958 | Buc | 558/394 |
| 3,496,213 | 2/1970 | Ross | 260/465 |
| 3,743,668 | 7/1973 | Scully | 558/394 |
| 3,943,162 | 3/1976 | Brennan et al. | 558/394 |

FOREIGN PATENT DOCUMENTS

| 1947933 | 4/1970 | Germany. | |
| 56974 | 3/1969 | Poland | 558/394 |
| 1256775 | 12/1971 | United Kingdom. | |
| 269162 | 6/1967 | U.S.S.R. | 558/394 |

OTHER PUBLICATIONS

J. Org. Chem., vol. 22, (1957), pp. 1213–1217; "Cupric acetate catalyzed monocyanoethylation of aromatic amines", S. A. Heininger.

Primary Examiner—Joseph Paul Brust
Attorney, Agent, or Firm—Sprung Horn Kramer & Woods

[57] ABSTRACT

A new process for the preparation of mono-N-β-cyanoethylanilines, characterized in that a substituted or unsubstituted aniline compound is reacted with acrylonitrile in the presence of active bleaching earth as catalyst at a temperature of between 80° and 200° C. in a nonaqueous reaction medium.

7 Claims, No Drawings

PROCESS FOR THE PREPARATION OF MONO-N-β-CYANOETHYLANILINES

The invention relates to a process for the preparation of mono-N-β-cyanoethylanilines.

Mono-N-β-cyanoethylanilines are important intermediates in the production of dyes, pharmaceuticals and crop protection agents. Although anilines do not react readily with acrylonitrile, there are already a number of processes for the preparation of mono-N-β-cyanoethylanilines. These processes, however, have certain disadvantages. For example, zinc chloride in U.S. Pat. No. 3,496,213, and copper acetate in A. Heininger J. org. Chem. 22 (1957) 1213, have been described as catalysts in the reaction of anilines with acrylonitrile, although these catalysts generate metal-containing effluent.

Glacial acetic acid is also known, from U.S. Pat. No. 2,492,972, as a catalyst in the cyanoethylization of anilines. However, this catalyst proves to be disadvantageous during separation from the reaction mixture.

The processes mentioned therefore have the disadvantage that, on the one hand, they entail waste disposal problems and/or are inconvenient to carry out and require corrosion-resistant materials.

The invention relates to a new process for the preparation of mono-N-β-cyanoethylanilines, characterized in that a substituted or unsubstituted aniline compound is reacted with acrylonitrile in the presence of active bleaching earth as catalyst at a temperature of between 80° and 200° C. in a nonaqueous reaction medium. The aniline compounds referred to are primary or secondary anilines which may be substituted one or more times on the ring.

In a preferred embodiment, anilines of the formula (I) are used

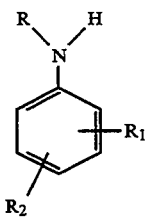

in which
R=hydrogen or optionally hydroxyl-substituted $C_1$-$C_{10}$-alkyl, and
$R_1$ and $R_2$=independently of one another H, $C_1$-$C_{10}$-alkyl or $C_1$-$C_{10}$-alkoxy.

In a particularly preferred embodiment, anilines of the formula (I) are used in which
R=hydrogen, methyl, ethyl, n-propyl, isopropyl, β-hydroxyethyl, β-hydroxypropyl or γ-hydroxypropyl,
$R_1$ and $R_2$=independently of one another hydrogen, methyl, ethyl, isopropyl, n-propyl, methoxy or ethoxy.

In a very particularly preferred embodiment, anilines of the formula (I) are used in which
R=hydrogen or methyl, in particular methyl,
$R_1$=hydrogen, methyl, methoxy or ethoxy and
$R_2$=hydrogen.

The term active bleaching earth refers in general to bleaching earths containing montmorillonite, such as, for example, bentonite, which have been activated by treatment with inorganic acids such as, for example, sulphuric acid or hydrochloric acid. Montmorillonites are described, for example, in Römpp Chemie Lexikon, 9th Edition, p. 2850, Georg Thieme Verlag, Stuttgart 1991. Particularly preference is given to bleaching earths which have been activated by treatment with hydrochloric acid, such as, for example, the bleaching earth of the Tonsil ® K 10 type from Südchemie.

In general, the active bleaching earths are obtained by treating bleaching earth with mineral acids. The acid is removed by filtration from the acidic suspension which is formed, and the filter cake is washed with water. The subsequent drying and grinding processes provide an active bleaching earth having a residual water content of less than 10%, preferably less than 7%.

The active bleaching earths generally have acid numbers of from 10 to 150, preferably from 10 to 80. In this context, the acid number indicates the number of mg of KOH which are consumed in the neutralization of 1 g of bleaching earth. It is generally determined by titration against an indicator such as phenolphthalein or Methyl Orange, or using a pH meter.

The molar ratio of the aniline compound to acrylonitrile is generally from 1.5:1 to 3.5:1, preferably from 2:1 to 3:1.

The term nonaqueous reaction medium generally denotes an organic reaction medium having a water content of not more than 0.5%, preferably of not more than 0.1%.

In a preferred embodiment, the aniline compound which is employed in a molar in the excess with respect to acrylonitrile serves simultaneously as the nonaqueous reaction medium, rendering an additional reaction medium unnecessary. The process is in general carried out at a temperature of from 80° to 200° C., preferably at from 100° to 150° C.

The quantity of catalyst to be employed is from 1 to 15% by weight, preferably from 2 to 6% by weight, based on the aniline compound.

The process is preferably carried out such that the aniline compound is heated together with the catalyst to the reaction temperature and the acrylonitrile is metered in slowly. The working-up of the reaction mixture is preferably carried out by removing the catalyst from the reaction mixture, preferably by filtration, at a suitable temperature and subjecting the catalyst-free reaction mixture to fractional distillation. This yields the starting compounds, acrylonitrile and the aniline compound, which can be employed again, and the mono-N-β-cyanoethylaniline, which is obtained in a purity of >99%.

Once removed by filtration, the catalyst can likewise be used again for the reaction.

The process according to the invention is carried out in a nonaqueous reaction medium and therefore produces no harmful effluents. It is simple to manage and gives pure products in a good yield.

The following examples illustrate the process according to the invention:

The catalyst used in the examples below is Tonsil ® K 10 from Südchemie. This catalyst is a bleaching earth in powder form, activated with hydrochloric acid and having the following physical characteristics:
Surface area: from 220 to 270 m²/g
Pore volume:

--- a) CCl₄
ml/g          0.318

| -continued | | | | |
|---|---|---|---|---|
| nm range | from 0 to 80 | | | |
| b) Hg porosimeter | | | | |
| ml/g | 0.29 | 0.53 | 0.13 | 0.07 |
| nm range | 15000–1750 | 1750–80 | 80–14 | 14–7.5 |

Loss on ignition: about 7%
Bulk density: from 300 to 370 g/l
Acid number: about 20

EXAMPLE 1

N-β-cyanoethyl-N-methylaniline 1071.5 Parts by weight (10 mol) of N-methylaniline and 15.0 parts by weight of Tonsil ® K 10 are placed in a 3-neck stirred flask fitted with a reflux condenser and inlet tube. The mixture is heated to 120° C. and 265.3 parts by weight (5 mol) of acrylonitrile are added at this temperature via the inlet tube. The reaction mixture is subsequently stirred for 18 hours at from 120° to 130° C. and then cooled to 60° C. The catalyst is filtered off and the liquid phase is subjected to fractional distillation. 47.7 parts by weight of acrylonitrile and 620.9 parts by weight of N-methylaniline are recovered and can be used again as starting material. The yield of N-β-cyanoethyl-N-methylaniline is 605.0 parts by weight ~75.5% conversion. The purity is 99.5% N-β-cyanoethyl-N-methylaniline.

EXAMPLE 2

N-β-Cyanoethyl-o-methoxyaniline 307.9 parts by weight of o-methoxyaniline and 12.0 parts by weight of Tonsil ® K 10 are initially introduced as described in Example 1, and then 66.3 parts by weight of acrylonitrile are added at 140° C. The mixture is stirred at 140° C. for 27 hours. After working up the mixture, the yield of N-β-cyanoethyl-o-methoxyaniline is 137.2 parts by weight ≈62.3% conversion. The purity of the worked-up product is 98.9% N-β-cyanoethyl-o-methoxyaniline.

EXAMPLE 3

N-β-Cyanoethyl-o-ethoxyaniline 342.9 parts by weight of o-ethoxyaniline and 12 parts by weight of Tonsil ® K 10 are initially introduced as described in Example 1, and then 66.3 parts by weight of acrylonitrile are added at from 140° to 155° C. The mixture is subsequently stirred at 170° C. for 27 hours. After working up the mixture, the yield of N-β-cyanoethyl-o-ethoxyaniline is 125.6 parts by weight ≈52.8% conversion, at a purity of 99.2%.

EXAMPLE 4

N-β-Cyanoethyl-o-methylaniline 214.4 parts by weight of o-methylaniline and 9.0 parts by weight of Tonsil ® K 10 are initially introduced as described in Example 1, and then 53.0 parts by weight of acrylonitrile are added at from 140° to 150° C. The mixture is subsequently stirred at 120° C. for 26 hours. After working up the mixture, the yield of N-β-cyanoethyl-o-toluidine is 58.6 parts by weight ≈36.6% conversion, at a purity of 98.7%.

What is claimed is:

1. A process for the preparation of N-β-cyanoethylanilines comprising reacting acrylonitrile with an aniline derivative of the formula:

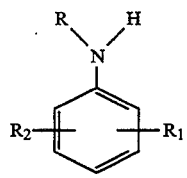

wherein

R represents hydrogen or optionally hydroxyl-substituted $C_{1-10}$-alkyl; and $R_1$ and $R_2$ independently represent hydrogen, $C_{1-10}$-alkyl or $C_{1-10}$-alkoxy;

said reaction being carried out at a temperature of between 80° and 200° C. in a nonaqueous medium and in the presence of a catalyst, wherein the catalyst is an activated bleaching earth, which contains montmorillonite, has been activated by treatment with an inorganic acid, has a residual water content of less than 10%, and has an acid number of from 10 to 150.

2. The process according to claim 1, wherein
R=hydrogen, methyl, ethyl, propyl, isopropyl, β-hydroxyethyl, β-hydroxypropyl or γ-hydroxypropyl,
$R_1$ and $R_2$=independently of one anther hydrogen, methyl, ethyl, isopropyl, propyl, methoxy or ethoxy.

3. The process according to claim 1, wherein
R=hydrogen or methyl,
$R_1$=hydrogen, methyl, methoxy or ethoxy and
$R_2$=hydrogen.

4. The process according to claim 1, wherein the catalyst is activated by treatment with hydrochloric acid.

5. The process according to claim 1, wherein from 1 to 15% by weight of catalyst based upon the aniline compound is employed.

6. The process according to claim 1, in which the molar ratio of the aniline compound to acrylonitrile is from 1.5:1 to 3.5:1.

7. The process according to claim 1, in which the aniline compound employed in a molar excess with respect to acrylonitrile is used as the nonaqueous reaction medium.

* * * * *